US012201411B1

(12) United States Patent
Moyer

(10) Patent No.: US 12,201,411 B1
(45) Date of Patent: *Jan. 21, 2025

(54) SYSTEMS, METHODS AND APPARATUS FOR GALVANIC SKIN RESPONSE MEASUREMENTS AND ANALYTICS

(71) Applicant: Kimchi Moyer, Cos Cob, CT (US)

(72) Inventor: Kimchi Moyer, Cos Cob, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/143,664

(22) Filed: May 5, 2023

Related U.S. Application Data

(63) Continuation of application No. 16/678,121, filed on Nov. 8, 2019, now Pat. No. 11,642,038.

(60) Provisional application No. 62/758,599, filed on Nov. 11, 2018.

(51) Int. Cl.
A61B 5/00 (2006.01)
A61B 5/0533 (2021.01)

(52) U.S. Cl.
CPC .......... A61B 5/0533 (2013.01); A61B 5/0022 (2013.01); A61B 5/4875 (2013.01); A61B 5/6825 (2013.01); A61B 5/6829 (2013.01); A61B 5/6843 (2013.01); A61B 5/7264 (2013.01); A61B 5/742 (2013.01); A61B 5/7475 (2013.01); A61B 5/748 (2013.01); A61B 2562/0215 (2017.08); A61B 2562/0219 (2013.01); A61B 2562/0247 (2013.01); A61B 2562/08 (2013.01)

(58) Field of Classification Search
CPC ... A61B 5/0533; A61B 5/0022; A61B 5/4875; A61B 5/6825; A61B 5/6829; A61B 5/6843; A61B 5/7264; A61B 5/742; A61B 5/7475; A61B 5/748; A61B 2562/0215; A61B 2562/0219; A61B 2562/0247; A61B 2562/08
See application file for complete search history.

(56) References Cited

U.S. PATENT DOCUMENTS

| 4,683,891 | A | * | 8/1987 | Cornellier | G16H 40/63 600/480 |
| 5,676,138 | A | * | 10/1997 | Zawilinski | A61B 3/113 600/301 |
| 5,830,140 | A | | 11/1998 | Dillinger et al. | |
| 6,167,299 | A | * | 12/2000 | Galchenkov | A61N 1/06 600/547 |

(Continued)

Primary Examiner — May A Abouelela
(74) Attorney, Agent, or Firm — NEO IP

(57) ABSTRACT

Systems, methods, apparatus, and non-transitory computer readable media for measuring and analyzing galvanic skin response. A system for measuring galvanic skin response includes an electrical conductivity meter (ECM) electrically connected to a positive electrode and a negative electrode and a server platform in network communication with the ECM. The ECM includes at least one processor and at least one memory. The positive electrode is in contact with a point on a hand or a foot of a subject. A circuit is created between the ECM and the subject including the positive electrode and the negative electrode. The positive electrode includes a pressure sensor to indicate an amount of pressure applied by a tip of the positive electrode on the point. The server platform includes artificial intelligence (AI) algorithms to detect variations in the pressure applied by the positive electrode during a session and/or across multiple sessions.

19 Claims, 11 Drawing Sheets

(56) References Cited

U.S. PATENT DOCUMENTS

| | | | |
|---|---|---|---|
| 6,743,182 B2* | 6/2004 | Miller | A61B 5/01 600/300 |
| 6,762,609 B2* | 7/2004 | Alanen | A61B 5/443 324/689 |
| 7,613,510 B2 | 11/2009 | Rentea et al. | |
| 7,693,579 B2* | 4/2010 | Hindinger | A61H 39/002 607/46 |
| 7,937,139 B2 | 5/2011 | Horne et al. | |
| 8,099,159 B2 | 1/2012 | Cook | |
| 8,131,355 B2* | 3/2012 | Clark | A61B 5/0531 600/547 |
| 8,332,027 B2* | 12/2012 | Larsen | A61H 39/002 600/548 |
| 8,682,425 B2 | 3/2014 | Larsen et al. | |
| 9,330,680 B2 | 5/2016 | Kassam et al. | |
| 9,788,794 B2* | 10/2017 | LeBoeuf | A61B 5/7239 |
| 9,888,884 B2 | 2/2018 | Chafe et al. | |
| 9,922,286 B1 | 3/2018 | Hazard | |
| 10,130,311 B1* | 11/2018 | De Sapio | A61B 5/7455 |
| 11,089,999 B1* | 8/2021 | Williams | A61B 5/4875 |
| 11,213,218 B2* | 1/2022 | Penning De Vries | G01N 27/041 |
| 2002/0059247 A1 | 5/2002 | Dillinger et al. | |
| 2004/0087838 A1* | 5/2004 | Galloway | G16H 40/63 600/300 |
| 2004/0143170 A1* | 7/2004 | DuRousseau | A61B 5/164 600/595 |
| 2005/0154264 A1* | 7/2005 | Lecompte | A61B 5/4884 128/920 |
| 2008/0077434 A1 | 3/2008 | Man et al. | |
| 2010/0222697 A1* | 9/2010 | Larsen | A61H 39/002 600/548 |
| 2011/0087337 A1* | 4/2011 | Forsell | A61N 1/37247 600/38 |
| 2015/0230726 A1 | 8/2015 | Greaves | |
| 2016/0066859 A1* | 3/2016 | Crawford | A61B 5/681 600/595 |
| 2017/0007847 A1 | 1/2017 | Gross et al. | |
| 2017/0105662 A1* | 4/2017 | Silawan | A61B 5/14542 |
| 2017/0164876 A1* | 6/2017 | Hyde | A61B 5/1118 |
| 2017/0196497 A1* | 7/2017 | Ray | G06N 7/01 |
| 2017/0238812 A1* | 8/2017 | Atlas | A61B 5/747 |
| 2017/0251967 A1* | 9/2017 | Premsukh | A61B 5/0004 |
| 2017/0273574 A1* | 9/2017 | Wu | A61B 5/02055 |
| 2017/0296121 A1* | 10/2017 | Dar | A61N 1/0484 |
| 2017/0322679 A1* | 11/2017 | Gordon | G06F 3/013 |
| 2017/0367614 A1* | 12/2017 | Zuckerman-Stark | A61B 5/02055 |
| 2018/0032126 A1* | 2/2018 | Liu | G06V 10/143 |
| 2018/0042813 A1 | 2/2018 | Chiang | |
| 2018/0085000 A1* | 3/2018 | Weffers-Albu | A61B 5/7282 |
| 2018/0121733 A1* | 5/2018 | Joshi | G06V 20/46 |
| 2018/0184735 A1* | 7/2018 | Longinotti-Buitoni | A61B 5/282 |
| 2018/0228434 A1* | 8/2018 | Dwarika | A61B 5/6801 |
| 2018/0229674 A1* | 8/2018 | Heinrich | A61B 5/18 |
| 2018/0314858 A1* | 11/2018 | Bertrand | G06F 21/64 |
| 2019/0064344 A1* | 2/2019 | Turner | G08B 21/02 |
| 2019/0175097 A1* | 6/2019 | Cowie | A61B 5/01 |
| 2019/0231249 A1* | 8/2019 | Dascalu | A61B 5/746 |
| 2019/0357831 A1* | 11/2019 | Avegliano | G16H 40/63 |
| 2019/0369728 A1* | 12/2019 | Rogers | G06T 19/006 |
| 2020/0138377 A1* | 5/2020 | Huijbregts | A61B 5/681 |
| 2020/0245869 A1* | 8/2020 | Sivan | G06N 3/08 |
| 2020/0288999 A1* | 9/2020 | Lasarov | A61B 5/0006 |
| 2021/0127975 A1* | 5/2021 | Rogers | A61B 5/0205 |
| 2021/0128055 A1* | 5/2021 | Bock | A61B 5/443 |
| 2021/0169425 A1* | 6/2021 | Dirkes | A61B 5/7221 |
| 2022/0100282 A1* | 3/2022 | Nocon | A63F 13/428 |

\* cited by examiner

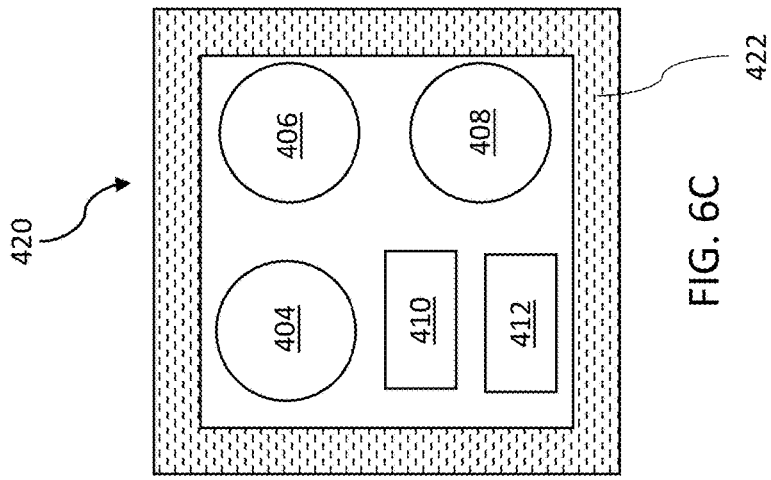
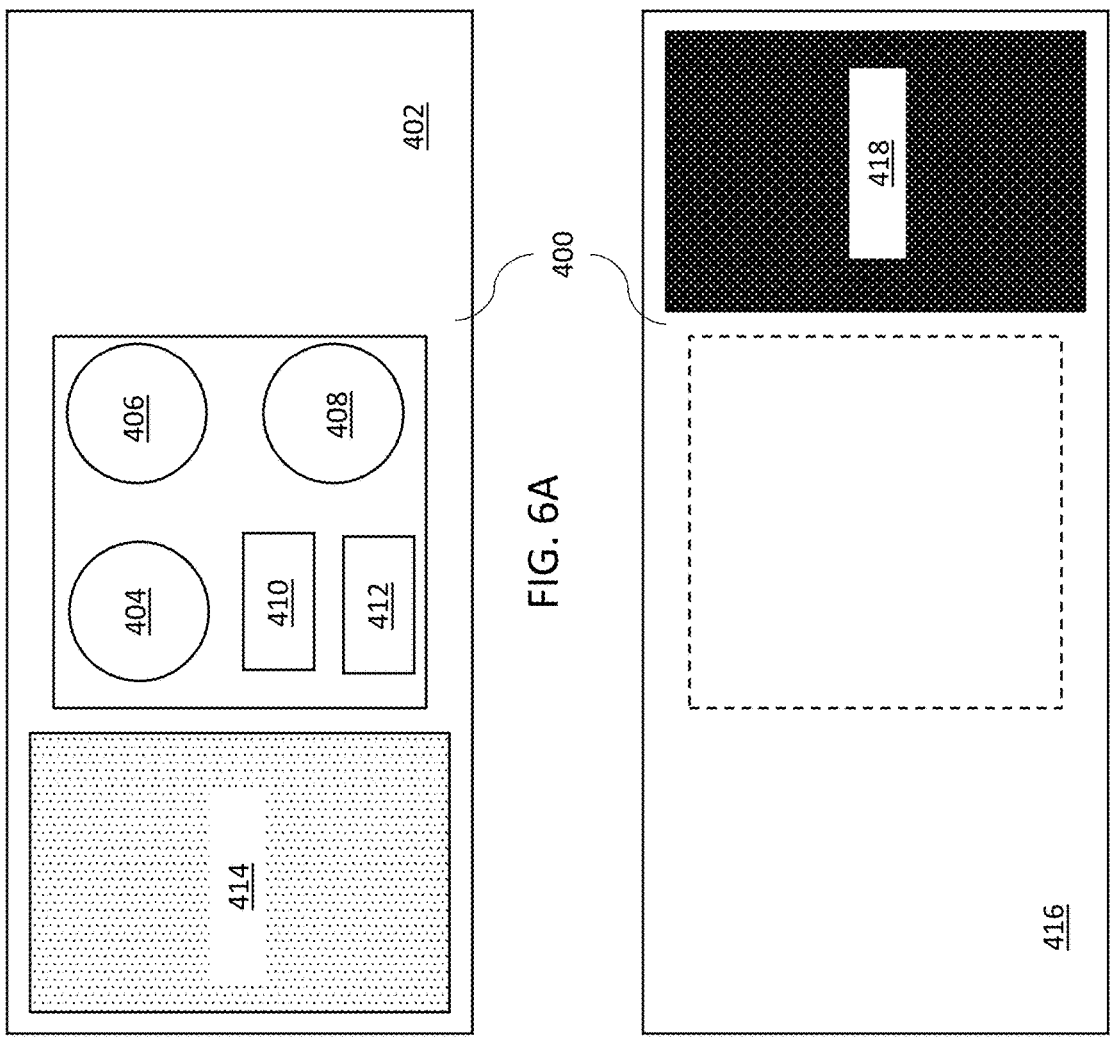

SYSTEMS, METHODS AND APPARATUS FOR GALVANIC SKIN RESPONSE MEASUREMENTS AND ANALYTICS

CROSS REFERENCES TO RELATED APPLICATIONS

This application relates to and claims priority from the following applications. This application is a continuation of U.S. application Ser. No. 16/678,121, filed Nov. 8, 2019, which claims priority to and the benefit of U.S. Provisional Patent Application No. 62/758,599, filed Nov. 11, 2018, each of which is incorporated herein by reference in its entirety.

BACKGROUND OF THE INVENTION

1. Field of the Invention

The present invention relates to devices, methods, and systems for measuring galvanic skin response.

2. Description of the Prior Art

It is generally known in the prior art to measure galvanic skin response. One application of galvanic skin response is to measure electrical properties of acupuncture points. Dr. Reinhard Voll, a German physician and engineer, developed a method of measuring galvanic skin response known as Electroacupuncture According to Voll (EAV) in the 1940s.

Representative prior art patent documents include the following:

U.S. Publication No. 20040087838 for meridian linking diagnostic and treatment system and method for treatment of manifested and latent maladies using the same by inventors Galloway, et al., filed Jul. 22, 2003 and published May 6, 2004, is directed to a computerized meridian linking diagnostic and treatment system that offers a new paradigm for practitioners in the EAV, GSR, EDS, and Meridian Stress Assessment fields. During the entire procedure, the present invention system outputs two permanent filters (frequencies) that link all of the body's meridians and stabilizes the data access points used for testing and carrying out the many functions of the present invention. The result is an interconnected meridian network linking the internal body systems to the data access points utilized by the system. The process begins by taking energetic readings at data access points. The computer stores the points that are the most stable. After the stable points are obtained, customized filters (frequencies) relating to specific issues or maladies (such as chemical toxins, allergies, digestion, etc.) are output or broadcast. Using only a single, but stable data access point as a reference point, if any of these filters creates a disturbance to any energetic component, cellular component, tissue, organ, or system of the body, each of which are linked by the interconnected meridian network, an imbalanced reading on the previously stable data access point will be created. The system will then automatically load products (remedies) that are useful for restoring homeostasis or balance. Each of the remedies are stored in the system database and can easily and quickly be scanned through until one or more products or remedies are discovered that will remove the underlying disturbance and allow the patient to obtain an improved level of health. The product/remedy is then placed in a holding tank that stores the results of each test. Specifically, the holding tank stores the filter(s) that created an imbalance/disturbance, the products (remedies) that allow the individual's body to restore homeostasis, balance, or improved health, and various prescription constraints that dictate administration of the products to the patient. The present invention also features several computer software functions, along with various methods of diagnosing maladies and treating a patient using an alternative medicine technique similar to a meridian stress assessment.

U.S. Publication No. 20080077434 for system and method for administration of on-line healthcare by inventors Man, et al., filed Jul. 15, 2005 and published Mar. 27, 2008, is directed to a healthcare administration system useful for the management of anamnesis and medical records, data analysis, guided diagnosis, medical treatment, and clinical investigation. The novel system comprising: a plurality of self-sufficient subsystems adapted to record, store, share, clinically investigate and analyze information by means of a common medical information protocol (CMIP); at least one end-unit device adapted to diagnose and/or treat patients, in communication with a subsystem for controlling, monitoring and recording the treatment process and its outcome by means of a medical protocol; at least one module adapted for a CMIP. The end-unit device is guided by the CMIP so that anamnesis, diagnosis and targeted treatment is dictated, provided, monitored, recorded and/or clinically investigated. The present invention also discloses a guided method for a healthcare administration system, useful for the management of medical records, data analysis, diagnosis, guided treatment and medical investigation by means of the medical system as defined above.

U.S. Pat. No. 7,613,510 for biofeedback device displaying results on a cellular phone display by inventors Rentea, et al., filed Dec. 11, 2003 and issued Nov. 3, 2009, is directed to biofeedback information measured at a body part of a user. The information is communicated to a cellular telephone device and used to produce a display on a display screen of the cellular telephone device.

U.S. Pat. No. 7,937,139 for systems and methods of utilizing electrical readings in the determination of treatment by inventors Horne, et al., filed Jul. 20, 2004 and issued May 3, 2011, is directed to a system for determining treatment options from at least two electrical readings. The electrical readings are conductivity measurements of a particular region on the human body. The system utilizes a correlation algorithm to determine the diagnosis which can easily be correlated with appropriate treatments. The correlation algorithm may include the analysis of multiple electrical readings in determining the diagnosis. The system may also utilize a database of clinical data to further assist in determining the diagnosis.

U.S. Pat. No. 8,099,159 for methods and devices for analyzing and comparing physiological parameter measurements by inventor Cook, filed Sep. 13, 2006 and issued Jan. 17, 2012, is directed to methods and devices that are capable of measuring physiological parameters of at least two contact points and determining whether the measured parameters reflect favorable or unfavorable physiological responses are disclosed herein. Specifically, the present invention encompasses a method that can non-invasively monitor physiological parameters of at least two contact points before and after a stimulus is applied to a subject and compare the measured parameters to determine whether the physiological state of the subject is favorable or unfavorable.

U.S. Pat. No. 8,131,355 for automated skin electrical resistance measurement device and method by inventor Clark, filed Aug. 1, 2007 and issued Mar. 6, 2012, is directed to an automated skin resistance measurement device having an applied signal selector for selecting one or more applied signal forms from an applied signal library, an applied signal generator in communication with the applied signal selector for generating one or more DC applied signals, each applied signal being in the form of a selected applied signal form, one or more applied signal applicators for administering the applied signals to test zones on the skin of a human subject, and one or more applied signal resistance sensors for sensing the resistance of the skin of the subject at the test zones.

U.S. Pat. No. 8,332,027 for electroacupuncture system and method for determining meridian energy balance number by inventor Larsen, filed May 12, 2010 and issued Dec. 11, 2012, is directed to an electroacupuncture system for measuring and treating meridian energy balance in a patient. The system also includes a processing apparatus connected to the electrical potential source capable of calculating an overall meridian energy balance number. The processing apparatus may be programmed to carry out a method for determining a meridian energy balance number.

U.S. Pat. No. 8,682,425 for electropuncture system by inventors Larsen, et al., filed Jan. 30, 2008 and issued Mar. 25, 2014, is directed to an electroacupuncture system for measuring and treating meridian energy balance in a patient. The system can include a pressure sensitive probe and return path contact, both of which are connected to an electrical potential source. The probe and contact are meant to be applied to a patient to diagnose and treat meridian energy imbalances. The system also includes a processing apparatus connected to the electrical potential source capable of interpreting the readings taken by the electrical potential source and probe and affecting operation of the system based on the readings. The processing apparatus may also use measurements to calculate an overall meridian energy balance number.

U.S. Publication No. 20150230726 for comprehensive health assessment tool for identifying acquired errors of metabolism by inventor Greaves, filed May 14, 2014 and published Aug. 20, 2015, is directed to a method of comprehensive health assessment includes using a biocommunication or bioenergetic device to measure signals sent across or through the body. Fluctuations in galvanic skin response are measured and transmitted to a computer or computing device and compared to a library of possible stimulus sources, each associated with a predetermined electrical signature.

U.S. Publication No. 20180042813 for smart equipment with bidirectional diagnosis and therapy device by inventor Chiang, filed Aug. 15, 2015 and published Feb. 15, 2018, is directed to a smart equipment with bidirectional diagnosis and therapy device, comprising a power supply unit used for providing each unit with required power, a high-voltage diagnosis and therapy unit provided for diagnosis and therapy as well as electronic acupuncture and sending back a diagnosis and therapy signal, an input and display unit provided for inputting operation commands and displaying related image, a wireless transmission unit provided for connecting to a cloud database wirelessly, a magnetic disk installed with program being loaded with application software for processing the diagnosis and therapy signal correspondingly, and a microprocessor used for processing related operation. Thereby, the present invention enables the user to manipulate the high-voltage diagnosis and therapy unit for diagnosis and therapy via the input and display unit according to suggestion from application software. Thus, correct diagnosis and therapy is allowed for the user to achieve the best effect.

SUMMARY OF THE INVENTION

The present invention relates to devices, methods, and systems for measuring and analyzing galvanic skin response.

It is an object of this invention to provide intelligent analytics and actionable data based on galvanic skin response measurements.

In one embodiment, the present invention includes a system for measuring galvanic skin response, including an electrical conductivity meter electrically connected to a positive electrode and a negative electrode, and a server platform in network communication with the electrical conductivity meter, wherein the electrical conductivity meter includes at least one processor and at least one memory, wherein the positive electrode is in contact with a point on a hand or a foot of a subject, wherein a circuit is created between the electrical conductivity meter and the subject including the positive electrode and the negative electrode, wherein the positive electrode includes a pressure sensor operable to indicate an amount of pressure applied by a tip of the positive electrode on the point, wherein the server platform includes a classification engine and a reasoning engine, and wherein the reasoning engine includes artificial intelligence (AI) algorithms operable to detect variations in the pressure applied by the positive electrode during a session and/or across multiple sessions.

In another embodiment, the present invention includes a system for measuring galvanic skin response, including an electrical conductivity meter electrically connected to a positive electrode and a negative electrode, and a server platform in network communication with the electrical conductivity meter, wherein the electrical conductivity meter includes at least one processor and at least one memory, wherein the positive electrode is in contact with a point on a hand or a foot of a subject, wherein a circuit is created between the electrical conductivity meter and the subject including the positive electrode and the negative electrode, wherein the positive electrode includes a pressure sensor operable to indicate an amount of pressure applied by a tip of the positive electrode on the point, wherein the positive electrode includes an accelerometer operable to measure an angle of the positive electrode, wherein the server platform includes a classification engine and a reasoning engine, and wherein the reasoning engine includes artificial intelligence (AI) algorithms operable to detect variations in the pressure applied by the positive electrode and variations in the angle of the positive electrode during a session and/or across multiple sessions.

In yet another embodiment, the present invention includes a system for measuring galvanic skin response, including an electrical conductivity meter electrically connected to a positive electrode and a negative electrode, a server platform in network communication with the electrical conductivity meter, at least one computing device in wired or wireless communication with the electrical conductivity meter and/or the server platform, and a hydration sensor operable to measure a level of hydration of a subject, wherein the electrical conductivity meter includes at least one processor, at least one memory, a display screen, a foot pedal operable to toggle between menu items displayed on the display screen, and a test plate, wherein the positive electrode is in contact with a point on a hand or a foot of the subject, wherein a circuit is created between the electrical conductivity meter and the subject including the positive electrode and the negative electrode, wherein the circuit further includes at least one element in contact with the test plate, wherein the test plate is formed of metal, wherein the test plate includes a plurality of cylindrical holes drilled in to the test plate operable to hold an ampule or a vial of the at least one element, wherein one or more of the at least one element is labeled with a bar code or a passive radio frequency identification (RFID) tag, wherein the electrical conductivity meter applies a measurement current of less than 12 µA, wherein the positive electrode has a brass or a silver tip, wherein the positive electrode includes a pressure sensor operable to indicate an amount of pressure applied by the tip of the positive electrode on the point, wherein the positive electrode includes an accelerometer operable to measure an angle of the positive electrode, wherein the server platform includes a classification engine and a reasoning engine, wherein the server platform also includes a historical database, a user library, an organ library, a problem library, and/or an element library, wherein the reasoning engine includes artificial intelligence (AI) algorithms operable to detect variations in the pressure applied by the positive electrode and variations in the angle of the positive electrode during a session and/or across multiple sessions, wherein the server platform is operable to calculate a compatibility score for the at least one element and the subject, wherein the compatibility score indicates a degree of effectiveness, a degree of sensitivity, a degree of tolerance, and/or a tendency to toxicity, wherein the server platform and/or the at least one computing device is operable to generate at least one report, wherein the at least one computing device includes a graphical user interface (GUI) operable to toggle between menu items, record testing data, display results, display recommended treatment plans, and/or display at least one report, and wherein the at least one element is a food, a food component, a beverage, a supplement, a medication, a drug, an herb, a spice, a vitamin, a mineral, a gemstone, a metal, an electronic device, a bodily fluid, a tissue, and/or a hair sample.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 6A illustrates a first side of a band electrode according to one embodiment of the present invention.

FIG. 6B illustrates a second side of the band electrode in FIG. 6A.

FIG. 6C illustrates a patch electrode according to one embodiment of the present invention.

DETAILED DESCRIPTION

Figure 1:
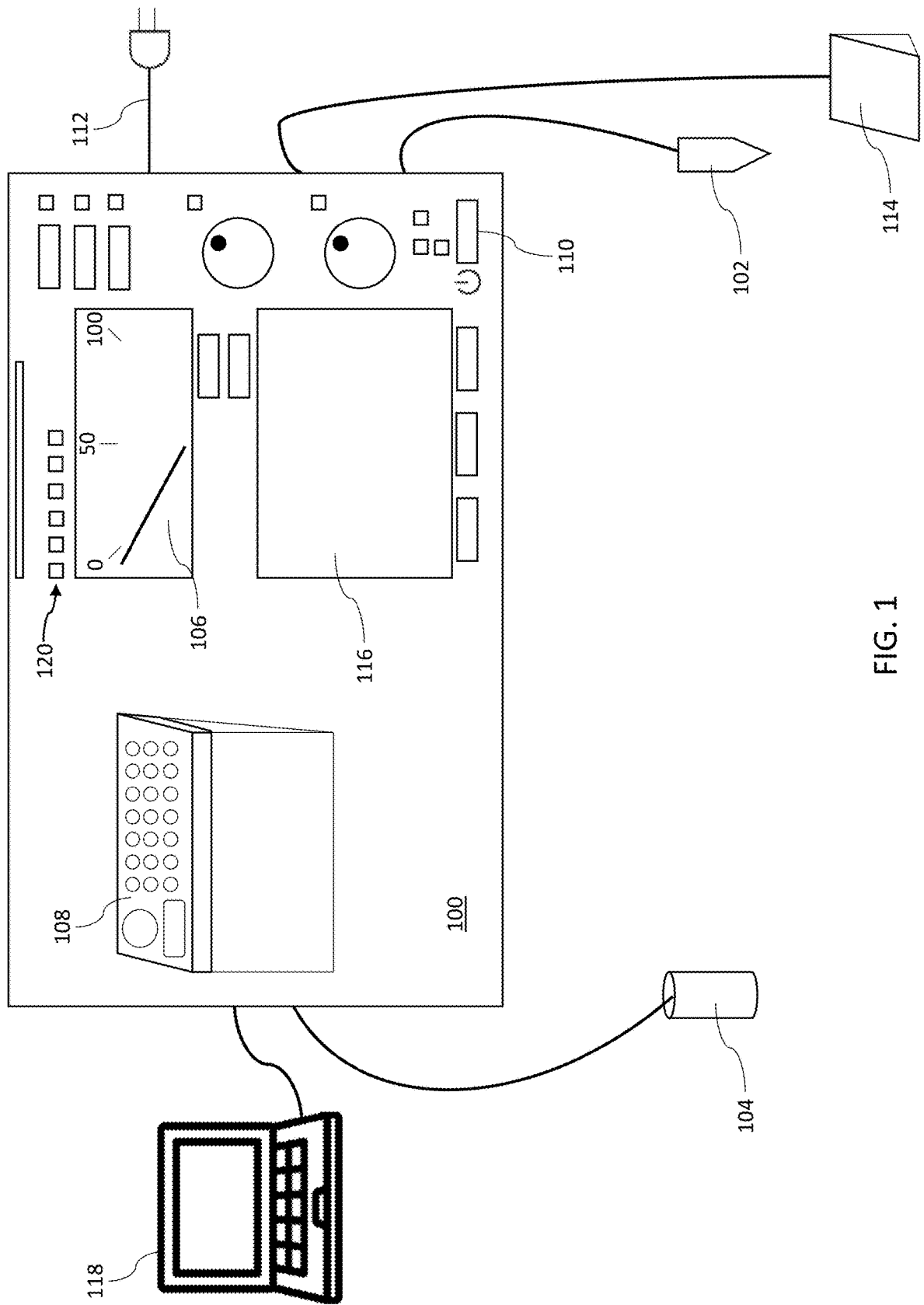
FIG. 1 illustrates one embodiment of an electrical conductivity meter.

The present invention is generally directed to galvanic skin response measurements and analytics.

In one embodiment, the present invention includes a system for measuring galvanic skin response, including an electrical conductivity meter electrically connected to a positive electrode and a negative electrode, and a server platform in network communication with the electrical conductivity meter, wherein the electrical conductivity meter includes at least one processor and at least one memory, wherein a circuit is created between the electrical conductivity meter and the subject including the positive electrode and the negative electrode, wherein the positive electrode is in contact with a point on a hand or a foot of a subject, wherein the positive electrode includes a pressure sensor operable to indicate an amount of pressure applied by a tip of the positive electrode on the point, wherein the server platform includes a classification engine and a reasoning engine, and wherein the reasoning engine includes artificial intelligence (AI) algorithms operable to detect variations in the pressure applied by the positive electrode during a session and/or across multiple sessions.

In another embodiment, the present invention includes a system for measuring galvanic skin response, including an electrical conductivity meter electrically connected to a positive electrode and a negative electrode, and a server platform in network communication with the electrical conductivity meter, wherein the electrical conductivity meter includes at least one processor and at least one memory, wherein the positive electrode is in contact with a point on a hand or a foot of a subject, wherein a circuit is created between the electrical conductivity meter and the subject including the positive electrode and the negative electrode, wherein the positive electrode includes a pressure sensor operable to indicate an amount of pressure applied by a tip of the positive electrode on the point, wherein the positive electrode includes an accelerometer operable to measure an angle of the positive electrode, wherein the server platform includes a classification engine and a reasoning engine, and wherein the reasoning engine includes artificial intelligence (AI) algorithms operable to detect variations in the pressure applied by the positive electrode and variations in the angle of the positive electrode during a session and/or across multiple sessions.

In yet another embodiment, the present invention includes a system for measuring galvanic skin response, including an electrical conductivity meter electrically connected to a positive electrode and a negative electrode, a server platform in network communication with the electrical conductivity meter, at least one computing device in wired or wireless communication with the electrical conductivity meter and/or the server platform, and a hydration sensor operable to measure a level of hydration of a subject, wherein the electrical conductivity meter includes at least one processor, at least one memory, a display screen, a foot pedal operable to toggle between menu items displayed on the display screen, and a test plate, wherein the positive electrode is in contact with a point on a hand or a foot of the subject, wherein a circuit is created between the electrical conductivity meter and the subject including the positive electrode and the negative electrode, wherein the circuit further includes at least one element in contact with the test plate, wherein the test plate is formed of metal, wherein the test plate includes a plurality of cylindrical holes drilled in to the test plate operable to hold an ampule or a vial of the at least one element, wherein one or more of the at least one element is labeled with a bar code or a passive radio frequency identification (RFID) tag, wherein the electrical conductivity meter applies a measurement current of less than 12 µA, wherein the positive electrode has a brass or a silver tip, wherein the positive electrode includes a pressure sensor operable to indicate an amount of pressure applied by the tip of the positive electrode on the point, wherein the positive electrode includes an accelerometer operable to measure an angle of the positive electrode, wherein the server platform includes a classification engine and a reasoning engine, wherein the server platform also includes a historical database, a user library, an organ library, a problem library, and/or an element library, wherein the reasoning engine includes artificial intelligence (AI) algorithms operable to detect variations in the pressure applied by the positive electrode and variations in the angle of the positive electrode during a session and/or across multiple sessions, wherein the server platform is operable to calculate a compatibility score for the at least one element and the subject, wherein the compatibility score indicates a degree of effectiveness, a degree of sensitivity, a degree of tolerance, and/or a tendency to toxicity, wherein the server platform and/or the at least one computing device is operable to generate at least one report, wherein the at least one computing device includes a graphical user interface (GUI) operable to toggle between menu items, record testing data, display results, display recommended treatment plans, and/or display at least one report, and wherein the at least one element is a food, a food component, a beverage, a supplement, a medication, a drug, an herb, a spice, a vitamin, a mineral, a gemstone, a metal, an electronic device, a bodily fluid, a tissue, and/or a hair sample.

Referring now to the drawings in general, the illustrations are for the purpose of describing one or more preferred embodiments of the invention and are not intended to limit the invention thereto.

As previously discussed, Dr. Reinhard Voll, a German physician and engineer, developed a method of measuring galvanic skin response known as Electroacupuncture According to Voll (EAV) in the 1940s. EAV is one application of measuring galvanic skin response. EAV utilizes principles of acupuncture based on meridians. EAV differs from traditional Chinese acupuncture in that there are 21 basic EAV meridians instead of 12 principal meridians. Acupuncture points on these meridians correspond to glands, internal organs, and/or subcomponents of internal organs. Electrical conductivity of the skin is higher on acupuncture points than on other locations. Dr. Helmut Schimmel improved EAV in the 1970s by utilizing a single acupuncture point instead of multiple points.

An electrical conductivity meter is used to measure galvanic skin response. An EAV device is one type of electrical conductivity meter. A practitioner tests a meridian point with a probe that corresponds to a positive electrode. The positive electrode is preferably a stylus with a brass or silver tip. A subject contacts (e.g., holds) a negative electrode. The practitioner tests the conductivity of a plurality of meridian points by contacting the skin of the subject with the positive electrode at a specific meridian point on the hands or feet. The negative electrode and positive electrode are electrically connected to the electrical conductivity meter (e.g., via cables). A small amount of current travels through the body when the positive electrode contacts the skin.

FIG. 1 illustrates one embodiment of an electrical conductivity meter. The electrical conductivity meter 100 is electrically connected to a probe 102 (i.e., positive electrode) and a negative electrode 104. A meter 106 displays a conductivity reading between 0 and 100. A test plate 108 is used to test at least one element. A power button 110 is used to turn the electrical conductivity meter 100 on or off. A power cord 112 connects the electrical conductivity meter 100 to alternating current (AC) power. Alternatively, the electrical conductivity meter is powered by at least one battery (e.g., rechargeable battery). A foot pedal 114 is optionally used to toggle between menu items displayed on a screen 116. In one embodiment, the screen is a touch screen. The electrical conductivity meter 100 is connected via a wired connection or a wireless connection to a computing device 118. The electrical conductivity meter 100 preferably has a pressure range indicator 120 to indicate a pressure exerted by the tip of the probe 102 on a surface (e.g., skin). Manuals for the VEGA BIO-expert and the WEGAMED Test Expert Plus include additional details regarding electrical conductivity meters, each of which is incorporated herein by reference in its entirety. Additional information regarding testing is included in the "Short Manual of the VEGATEST-method" by Fehrenbach et al., including both the $2^{nd}$ ed. (1986) and SKU no. FLIT0.13059, available at https://www.wegamed.de/product/short-manual-of-the-vegatest-method-2/, each of which is incorporated herein by reference in its entirety.

The probe preferably includes a pressure sensor to indicate an amount of pressure exerted by the tip of the probe on a surface. In another embodiment, the probe includes a three-dimensional (3D) accelerometer to measure a position (e.g., angle) of the probe. Alternatively or additionally, the probe includes a 3D gyroscope to measure a position or angle of the probe.

The electrical conductivity meter preferably includes at least one processor. By way of example, and not limitation, the at least one processor is a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof operable to perform calculations, process instructions for execution, and/or otherwise manipulate information. In one embodiment, one or more of the at least one processor is operable to run predefined programs stored in at least one memory of the electrical conductivity meter.

The electrical conductivity meter preferably includes at least one antenna, which allows the electrical conductivity meter to transmit data to at least one computing device (e.g., smartphone, tablet, laptop computer, desktop computer). In a preferred embodiment, the electrical conductivity meter is in wireless network communication with the at least one computing device. The wireless communication is, by way of example and not limitation, radio frequency (RF), BLUETOOTH, ZIGBEE, WI-FI, wireless local area networking, near field communication (NFC), or other similar commercially utilized standards. Alternatively, the at least one computing device is in wired communication with the control unit through universal serial bus (USB), FIREWIRE, or equivalent. The electrical conductivity meter is operable to receive data (e.g., program updates) from the at least one computing device and/or a server platform.

Figure 2:
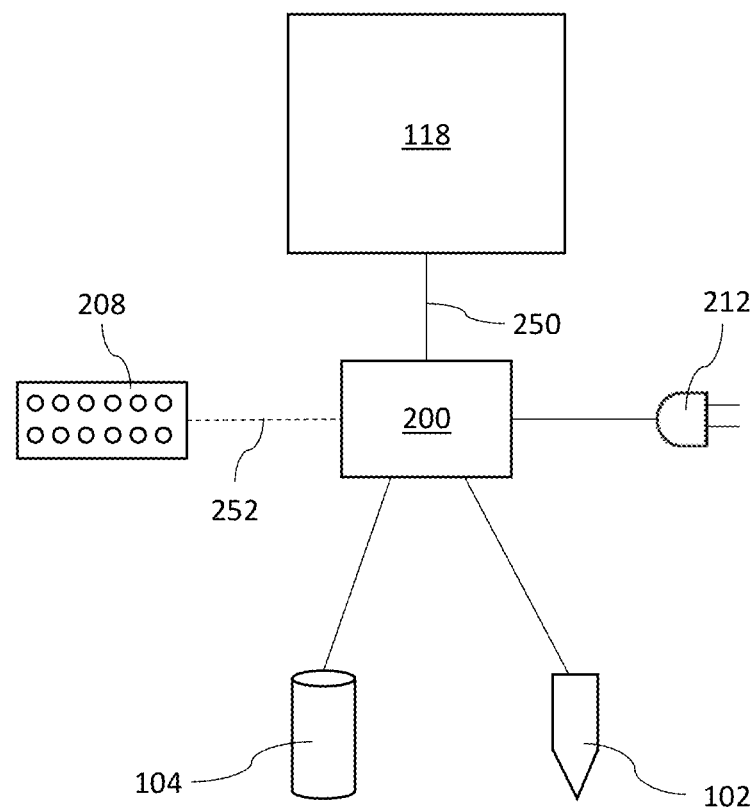
FIG. 2 illustrates another embodiment of an electrical conductivity meter.

FIG. 2 illustrates another embodiment of an electrical conductivity meter. In this embodiment, the electrical conductivity meter 200 is connected via a wired connection (e.g., cable 250) to the computing device 118 (e.g., smartphone, tablet, laptop computer, desktop computer). A power cord 212 connects the electrical conductivity meter 200 to alternating current (AC) power. Alternatively, the electrical conductivity meter is powered by at least one battery (e.g., rechargeable battery). The electrical conductivity meter 200 is connected to the probe 102 and the negative electrode 104. A test plate 208 is selectively added or removed to the electrical conductivity meter 200 via a test plate cable 252. Advantageously, the electrical conductivity meter 200 provides for greater portability than the electrical conductivity meter shown in FIG. 1 due to its modular nature and use of at least one processor on the computing device.

Figure 3A:
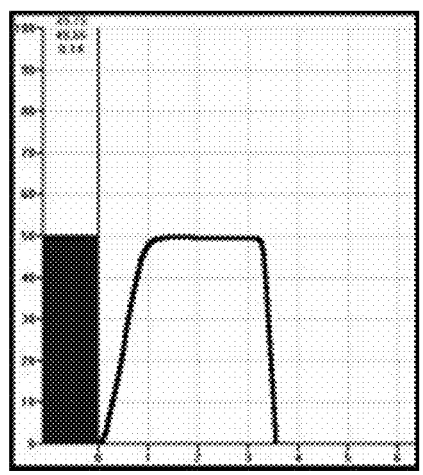
FIG. 3A illustrates a conductivity reading of a balanced meridian.
Figure 3B:
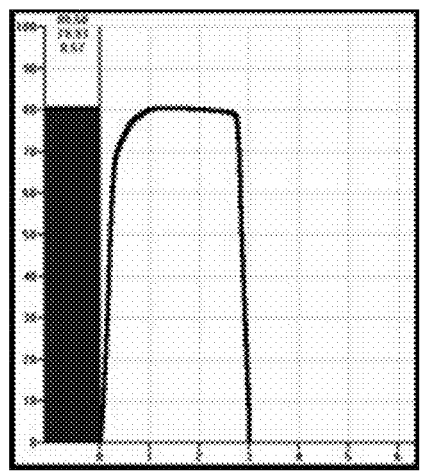
FIG. 3B illustrates a conductivity reading of an irritated or inflamed meridian.
Figure 3C:
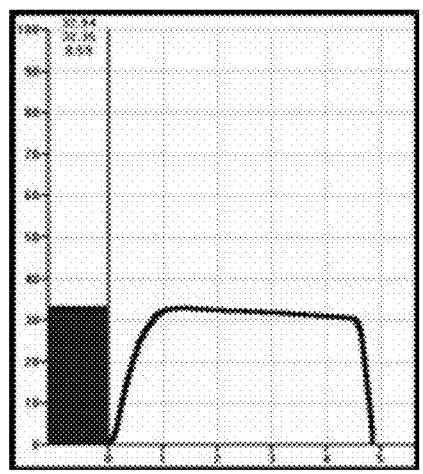
FIG. 3C illustrates a degenerated or impaired meridian.

An electrical conductivity meter uses a voltage of less than 1.5V and a measurement current of less than 12 µA. In a preferred embodiment, the electrical conductivity meter uses a voltage of 1.5V and a measurement current of 10 µA. The electrical conductivity meter is calibrated to give a conductivity reading of 0 to 100. A balanced meridian has a conductivity reading of 50 or approximately 50 as shown in FIG. 3A. A conductivity reading greater than 50 or greater than approximately 50 (e.g., >55) indicates irritation or inflammation of the meridian as shown in FIG. 3B. Inflamed tissue swells with water, which results in a higher electrical conductivity. A conductivity reading less than 50 or less than approximately 50 (e.g., <45) indicates degeneration or impairment of the meridian as shown in FIG. 3C. A chronically impaired organ becomes harder and loses hydration, which results in a lower electrical conductivity.

Figure 4:
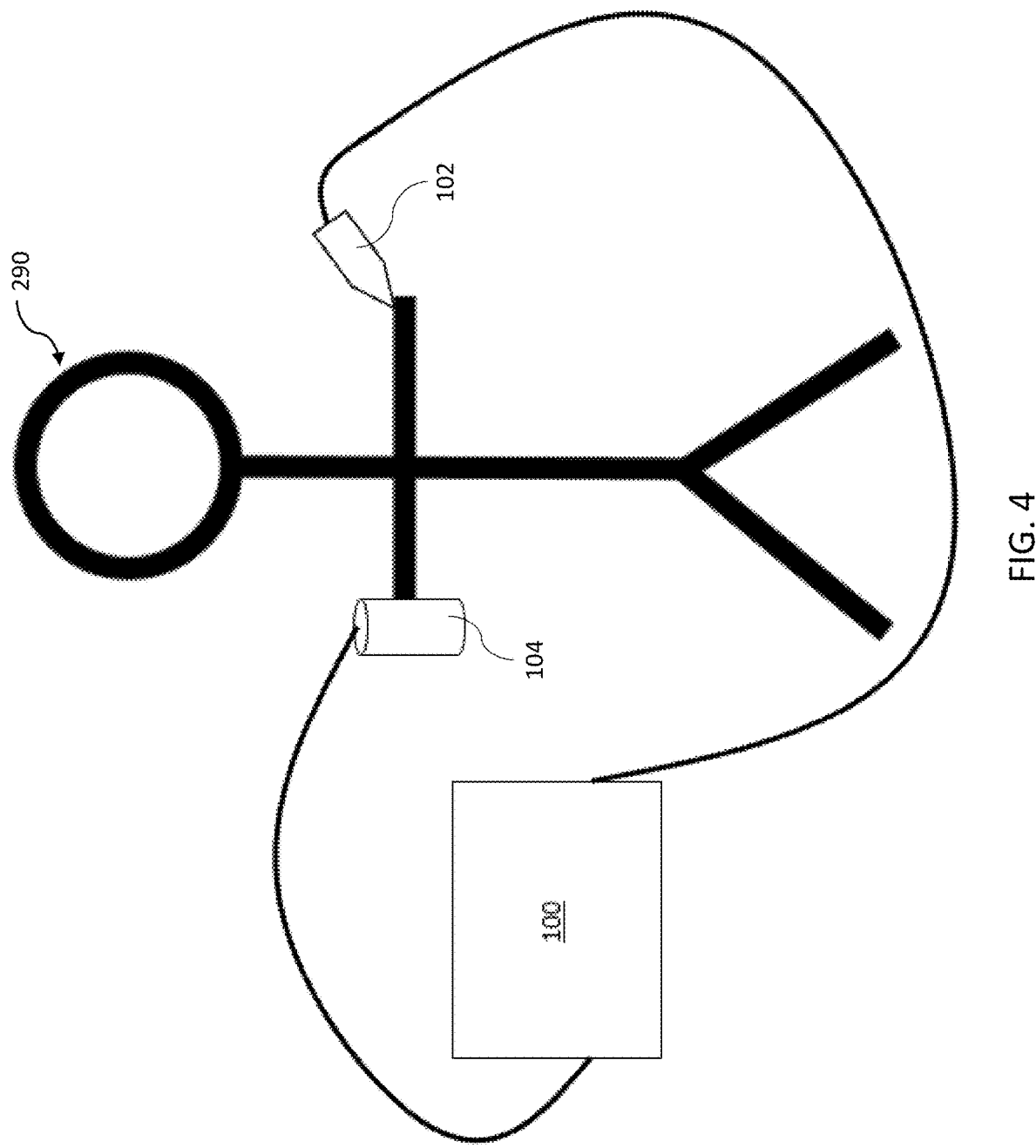
FIG. 4 illustrates a circuit created between a subject and an electrical conductivity meter according to one embodiment of the present invention.

FIG. 4 illustrates a circuit created between a subject and an electrical conductivity meter. As previously described, the electrical conductivity meter 100 is connected to a probe 102 (i.e., positive electrode) and a negative electrode 104. The probe 102 is shown contacting a subject 290 on a first hand. A second hand of the subject 290 is holding the negative electrode 104. Touching the probe 102 to the first hand while the subject 290 holds the negative electrode 104 creates a circuit. In another embodiment, the circuit also includes at least one element (e.g., food, beverage, supplement) on the test plate of the electrical conductivity meter.

Figure 5:
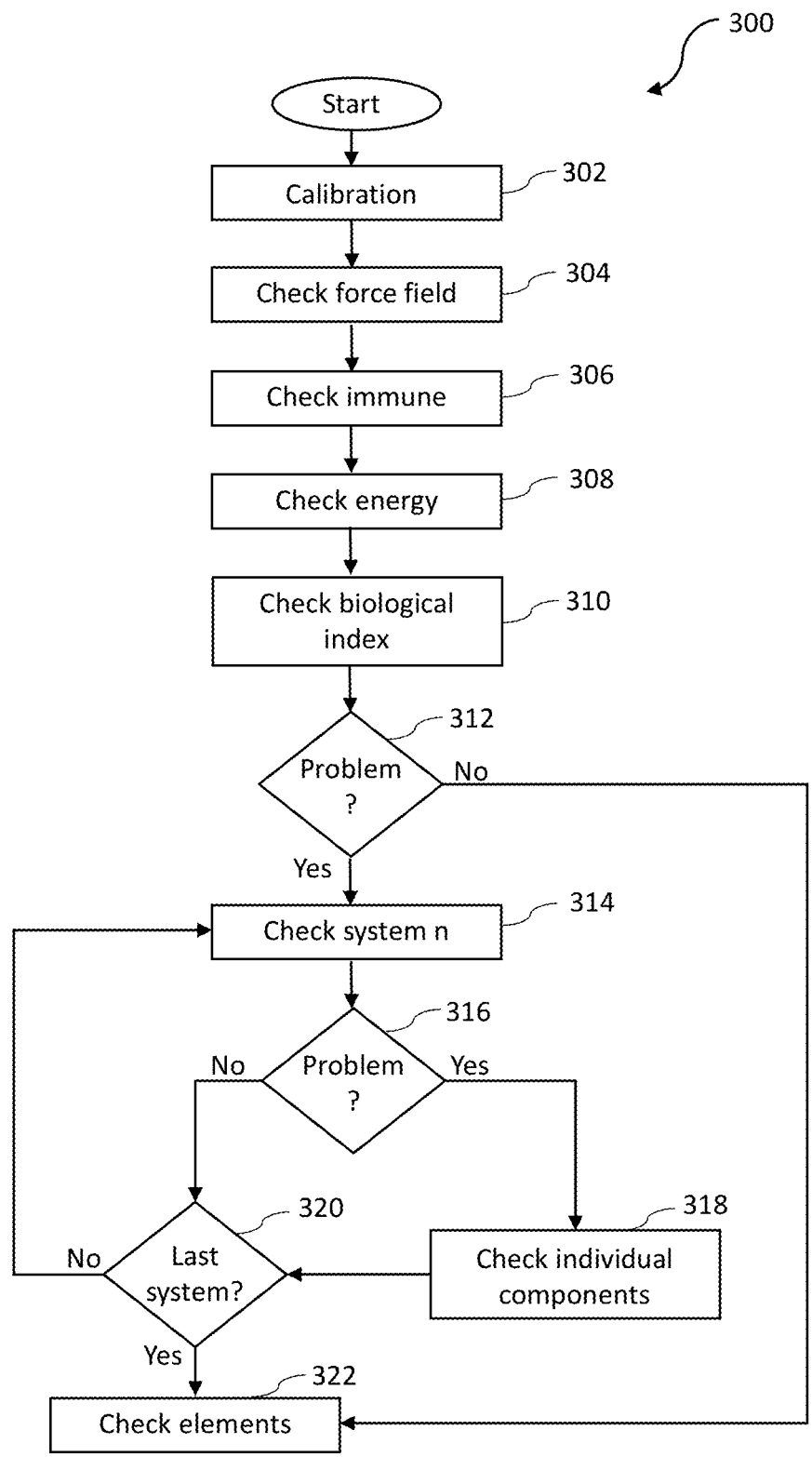
FIG. 5 is a flow chart detailing a method of calibrating and testing using the electrical conductivity meter according to one embodiment of the present invention.

FIG. 5 is a flow chart detailing a method of calibrating and testing using the electrical conductivity meter. The method 300 includes a step of calibrating 302 the electrical conductivity meter. The calibration includes setting a noise threshold and determining whether signals need to be amplified. After calibration, the method 300 includes a step 304 of checking a force field of the subject, a step 306 of checking an immune system of the subject, and a step 308 of checking an energy level of the subject. Steps 304-308 create a baseline for the reading.

A biological index of the subject is measured in step 310. The biological index is preferably a characteristic of the mesenchyme (i.e., connective tissue). The connective tissue reflects a biological age of a subject. In a preferred embodiment, the biological index includes numbers between 1 and 21, wherein lower numbers (e.g., 1) correspond to younger biological age and higher numbers (e.g., 21) correspond to higher biological age. In another embodiment, a biological index value of 15 or greater reflects a health problem.

In step 312, it is determined whether there is a problem with the biological index of the subject (e.g., value >15). If there is not a problem with the biological index, the method 300 proceeds to step 322. If there is a problem with the biological index, a biological subsystem of a plurality of biological subsystems is checked in step 314. After the measurement of the biological subsystem, it is determined whether there is a problem with the biological subsystem (e.g., conductivity reading >55, conductivity reading <45) in step 316. If there is a problem with the biological subsystem, individual components within the biological subsystem are checked for problems in step 318. The problems include, but are not limited to, increased acidity, presence of at least one bacterium, presence of at least one virus, and imbalance of yeast. After all individual components within the biological subsystem are checked for problems, it is determined in step 320 whether the biological subsystem tested in step 314 was the final biological subsystem. If there was not a problem with the biological subsystem in step 316, the method 300 proceeds to step 320. If the biological subsystem was not the final biological subsystem, the method 300 returns to step 314. If the biological subsystem was the final biological system, at least one element is tested in step 322.

To test reactions to different elements, at least one element is placed in contact with a test plate (e.g., placed in and/or on a test plate) to put the at least one element in circuit with the subject. The test plate is preferably formed of metal. In a preferred embodiment, the test plate includes a plurality of cylindrical holes drilled into the test plate. Each of the plurality of cylindrical holes is operable to hold an ampule or a vial of an element to be tested.

The at least one element includes, but is not limited to, a food, a food component (e.g., coloring, additive, preservative, thickener, stabilizer, emulsifier, enhancer), a beverage, a supplement, a medication, a drug, an herb, a spice, a vitamin, a mineral, a gemstone, a metal, an electronic device, a bodily fluid, a tissue, and/or a hair sample. The test plate allows for one or more of the at least one element to be selectively added or selectively removed from the circuit.

In a preferred embodiment, the ampule or the vial containing the at least one element is labeled to identify its contents. In one embodiment, the ampule or the vial is labeled with a barcode. Alternatively, the ampule or the vial is labeled with a passive radio frequency identification (RFID) tag. In one embodiment, a scanner for the label is connected via a cable (e.g., USB, FIREWIRE, or equivalent) to the electrical conductivity meter. Alternatively, the scanner is built into the electrical conductivity meter.

In yet another embodiment, an element library is used to store digital signatures of at least one element. An algorithm compares a conductivity reading with the digital signatures of the at least one element to determine whether a response to the at least one element is positive, negative, or neutral. Advantageously, this allows for the at least one element to be tested without placing a sample of the at least one element on a test plate.

In one embodiment, an electrical conductivity meter is in network communication with a server platform via a computing device. The computing device is in wired or wireless communication with the electrical conductivity meter. The computing device is installed with at least one application program operable to provide a graphical user interface (GUI) operable for toggling between menu items (e.g., different steps), recording testing data at different steps, and display diagnostic results and recommended treatment plans.

In one embodiment, the present invention provides a smart electrical conductivity meter in direct network communication with a server platform. An example of a smart electrical conductivity meter is shown in FIG. 2. The smart electrical conductivity meter comprises a computing module, a communication module, and a display module. The computing module is operable to collect and process data from a testing circuit. The communication module is operable to communicate with a server platform. The display module comprises a GUI. In one embodiment, the smart electrical conductivity meter is a smartphone, a tablet, a laptop, and/or any other portable device, installed with an application program in network communication with a server platform.

In one embodiment, the present invention provides a circuit toolkit including at least one signal sensor device (e.g., electrodes, bands embedded with sensors), a testing plate, and an adapter module. An example of the circuit toolkit is shown in FIG. 2. The adapter module connects the testing plate, the two electrodes, and a subject into a circuit, and transmits data signals to the electrical conductivity meter.

In one embodiment, at least one electrode is configured as a patch or a band wrapping around a finger portion which includes an acupuncture point. The patch or the band includes a galvanic skin sensor to contact the acupuncture point of a subject. In one embodiment, the patch or the band is embedded with a pressure sensor to measure and display the pressure of the band on the finger to make sure the pressure is in an acceptable range. In another embodiment, the patch or the band includes a hydration sensor to measure a level of hydration of the subject. Advantageously, eliminating variability in pressure of the probe and/or the location of the probe gives more accurate results and more consistent results between practitioners. Additionally, using the patch or the band frees a practitioner's hands to run the electrical conductivity meter and/or the computing device. In one embodiment, the patch or the band further includes a computing module in communication with the hydration sensor, the pressure sensor, and the galvanic skin sensor. The computing module comprises an Artificial Intelligence (AI)-based algorithm to learn the patterns of the hydration data and automatically calculates the optimal pressure for the galvanic skin sensor so as to obtain accurate testing results for a subject. Hydration data is alternatively used to normalize conductivity readings of meridians, as the hydration level of the skin affects the conductivity of skin. In another embodiment, a moisture and/or salinity sensor in the band electrode measures an amount of moisture and/or concentration of sodium in the moisture at the contact point between the band electrode and the skin and normalizes conductivity readings based on these measurements.

FIG. 6A illustrates a first side 402 of a band electrode 400 according to one embodiment of the present invention. The first side 402 includes a galvanic skin sensor (e.g., probe) 404, a hydration sensor 406, and a pressure sensor 408. The first side 402 preferably includes a computing module 410 (e.g., microprocessor) and/or an antenna 412. The computing module 410 is operable to perform calculations using data from the galvanic skin sensor 404, the hydration sensor 406, and/or the pressure sensor 408. Alternatively, data from the galvanic skin sensor 404, the hydration sensor 406, and/or the pressure sensor 408 is calculated on the electrical conductivity meter and/or the server platform. The antenna 412 is operable to wirelessly transmit (e.g., via BLUETOOTH, NFC, RF, RFID, WI-FI) data to the electrical conductivity meter and/or the server platform. Alternatively, data from the galvanic skin sensor 404, the hydration sensor 406, and/or the pressure sensor 408 is transmitted via a wired connection to the electrical conductivity meter and/or the server platform. The first side 402 also includes hook tape 414.

FIG. 6B illustrates a second side 416 of the band electrode 400 in FIG. 6A. The second side 416 includes loop tape 418. In another embodiment, the first side includes loop tape and the second side includes hook tape. Alternatively, the band electrode is secured using an adhesive or an elastic.

FIG. 6C illustrates a patch electrode 420 according to one embodiment of the present invention. The patch electrode 420 includes a galvanic skin sensor (e.g., probe) 404, a hydration sensor 406, and a pressure sensor 408. The first side 402 preferably includes a computing module 410 (e.g., microprocessor) and/or an antenna 412. The computing module 410 is operable to perform calculations using data from the galvanic skin sensor 404, the hydration sensor 406, and/or the pressure sensor 408. Alternatively, data from the galvanic skin sensor 404, the hydration sensor 406, and/or the pressure sensor 408 is calculated on the electrical conductivity meter and/or the server platform. The antenna 412 is operable to wirelessly transmit (e.g., via BLUETOOTH, NFC, RFID, WI-FI) data to the electrical conductivity meter and/or the server platform. Alternatively, data from the galvanic skin sensor 404, the hydration sensor 406, and/or the pressure sensor 408 is transmitted via a wired connection to the electrical conductivity meter and/or the server platform. The patch electrode 420 includes an adhesive 422 for attachment to the skin.

In one embodiment, the application program installed on the smart electrical conductivity meter includes a GUI to facilitate operations, and a computing module for data collection and packaging.

In one embodiment, the smart electrical conductivity meter comprises a camera operable to capture images of the testing circuit. The server platform is operable to process the captured images based on an AI/machine learning algorithm and detect any defects in the circuit and send warnings and/or suggestions to the user for correction. In one embodiment, the smart electrical conductivity meter includes an AI-powered virtual assistant to verbally instruct the user for self-testing. The AI-power virtual assistant understands natural language voices, converses with the user, and executes voice commands.

In one embodiment, the server platform comprises a database storing historical data from tested subjects. The database is continuously updated with new obtained data. The historical data includes subject profile data, baseline data, diagnostic data and treatment data of tested subjects. The subject profile data includes gender, sex, age, race, and/or medical history (e.g., conditions, medications, nutritional supplements, weight, body mass index (BMI)) of a tested subject. The baseline data includes force field data, immunity data, energy level data, and volume control data for a tested subject pre-treatment and post-treatment.

In one embodiment, the server platform includes a proprietary organ library. In another embodiment, the server platform is operable to access a third-party organ library via an Application Program Interface (API).

In one embodiment, the server platform includes a proprietary problem library. The proprietary problem library includes different problem models for a specific organ. In one embodiment, problems in a specific organ include, but are not limited to, increased acidity, presence of at least one bacterium, presence of at least one virus, and imbalance of yeast.

In one embodiment, the server platform includes a proprietary element library. The element library includes biosignature data for different types of food and other elements mentioned before. The server platform is operable to update the element library with new elements introduced to the market. In one embodiment, the server platform comprises a modeling engine operable to build a virtual element based on a machine learning algorithm. The machine learning algorithm is operable to continuously extract data regarding new elements from various database and/or data sources. The modeling engine is operable to automatically build a virtual element based on collected data. In another embodiment, the modeling engine is operable to build a virtual element based on data input by a user via a GUI. In one embodiment, the server platform is operable to access to a third-party element library via an API.

In one embodiment, the server platform comprises a classification engine operable to classify the historical data and incoming data from tested subjects. The classification is based on gender, age range, race, organs, etc.

In one embodiment, the server platform comprises a reasoning engine built with artificial intelligence (AI) algorithms. The reasoning engine is operable to generate a reasoning model based on multiple sets of training data. The multiple sets of training data are a subset of historical data. For example, a subject's health condition is significantly improved after a specific treatment for a predetermined period of time. The training data includes context data (e.g., baseline data, testing data) and action data (e.g., treatment data). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

In another embodiment, the AI algorithms are operable to detect variations in pressure applied by a practitioner during a session and/or across multiple sessions (e.g., single subject with multiple sessions, multiple subjects). In yet another embodiment, the AI algorithms are operable to detect variations in an angle of the probe. Pressure applied by the practitioner and the angle of the probe can both affect the conductivity readings. Advantageously, this allows the AI algorithms to detect and address bias both within a session for a single subject and over time with multiple subjects. For example, the AI algorithms are operable to detect if the practitioner tends to lower the angle of the probe towards the end of sessions for all subjects, indicating that the practitioner is fatigued and/or not focused after 45 minutes. Additionally, AI algorithms are operable to address differences in hydration determined via a hydration sensor of a single subject within a single session or for a single subject or multiple subjects over multiple sessions. In another embodiment, AI algorithms detect and account for differences in moisture or salinity at the contact point between the band electrode and the skin of a single subject over one session or multiple sessions or for multiple subjects over multiple sessions.

The server platform is preferably operable to generate at least one report (e.g., organ report, element test report, treatment report, progress report). Alternatively, the at least one computing device is operable to generate the at least one report.

In one embodiment, the reasoning model is operable to generate a treatment plan for a subject based on the test results. The test results include organ reports and element test reports. The organ reports include conductivity readings for organs and identified problems for organs with conductivity readings greater than 50. The element test reports include conductivity readings and biometric index scores corresponding to different types of elements (e.g., food, food component, beverage, supplement, medication, drug, herb, spice, vitamin, mineral, gemstone, metal, electronic device, bodily fluid, tissue, hair sample).

In one embodiment, the server platform comprises an optimization engine to optimize an overall treatment plan for a subject to get maximum effectiveness when more than one problem organ is detected so that the treatment plan is good for all the problem organs, or at least certain treatments good for one problem organ do not worsen other problem organs.

Figure 7A:
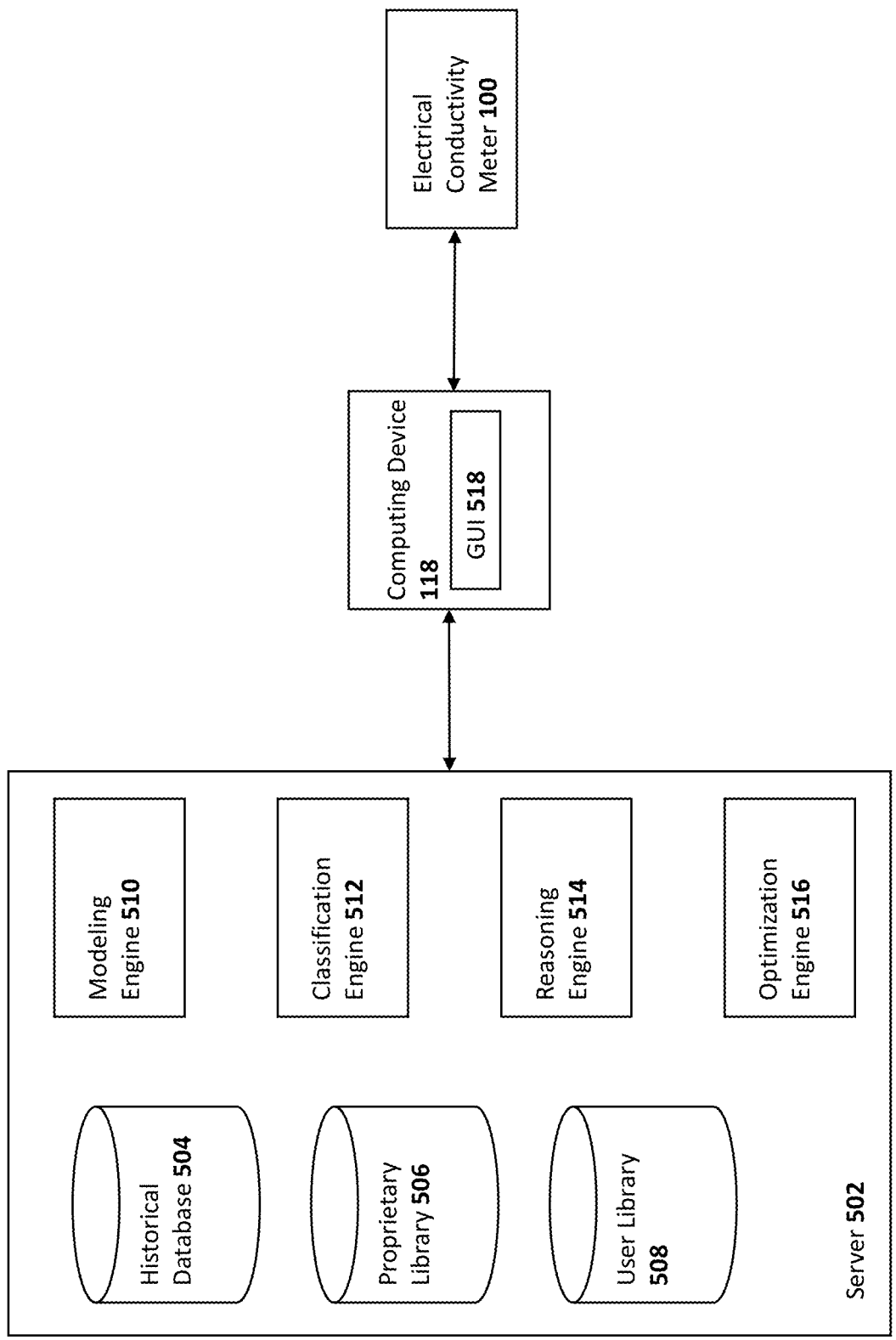
FIG. 7A is a diagram of a server platform in network communication with an electrical conductivity meter via a computing device according to one embodiment of the present invention.

FIG. 7A is a diagram of a server platform 502 in network communication with an electrical conductivity meter 100 via a computing device 118 according to one embodiment of the present invention. The server 502 incudes a historical database 504, a proprietary library 506, a user library 508, a modeling engine 510, a classification engine 512, a reasoning engine 514, and an optimization engine 516. The computing device 118 includes a GUI 518.

Figure 7B:
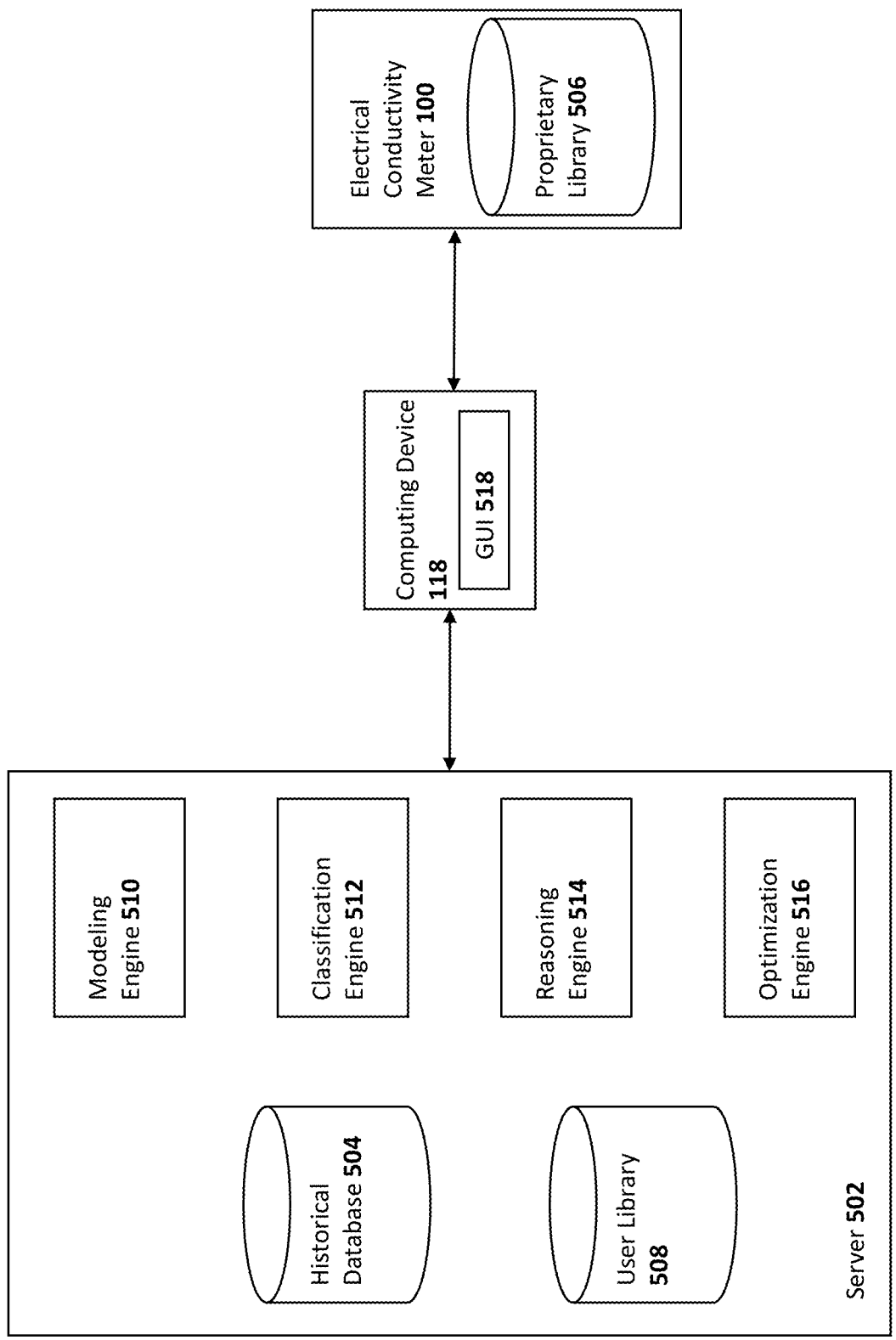
FIG. 7B is a diagram of a server platform in network communication with an electrical conductivity meter via a computing device according to one embodiment of the present invention.

FIG. 7B is a diagram of a server platform 502 in network communication with an electrical conductivity meter 100 via a computing device 118 according to another embodiment of the present invention. FIG. 7B differs from FIG. 7A in that the proprietary library 506 is on the electrical conductivity meter 100 rather than on the server 502.

Figure 8:
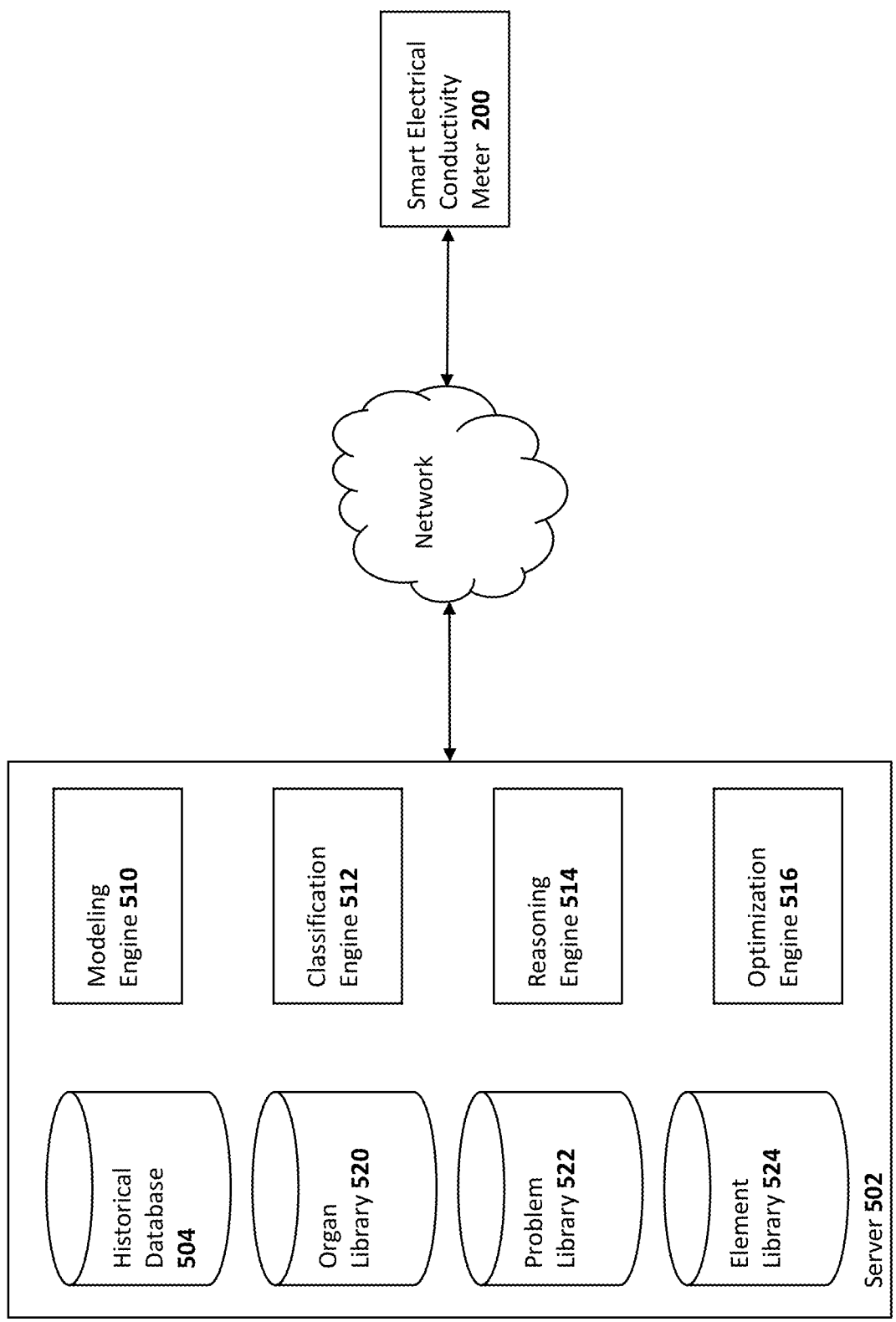
FIG. 8 is a diagram of a server platform in network communication with a computing device configured as a smart electrical conductivity meter according to one embodiment of the present invention.

FIG. 8 is a diagram of a server platform 502 in network communication with a computing device configured as a smart electrical conductivity meter 200 according to one embodiment of the present invention. The server 502 incudes a historical database 504, an organ library 520, a problem library 522, an element library 524, a modeling engine 510, a classification engine 512, a reasoning engine 514, and an optimization engine 516.

In one embodiment, the server platform is operable to automatically scan each subsystem of a subject based on the organ library and generate an organ report for the subject. The organ report includes conductivity readings for all organs. Problem organs are identified with conductivity readings larger than a threshold. In one embodiment, the threshold is 50, 55, 60, 65, or 70. Potential problems are identified for the problem organs as well. The server platform is also operable to automatically test a category of elements based on the element library and generate an element test report. The element test report comprises conductivity readings and biometric index scores corresponding to the test elements, comparing to the baseline conductivity reading and baseline biometric index score of the subject.

In one embodiment, the server platform is operable to generate a treatment report based on the organ report and the element test report of a subject. The treatment report includes elements beneficial for the subject and elements to be avoided and/or limited by the subject.

In another embodiment, the server platform is operable to generate a progress report. The progress report displays historical changes in the organ report and/or the element test report over time.

In one embodiment, the server platform provides licensed access via an API. An application program is downloaded and installed on a computing device. A user account is created based on the type of the user (e.g., enterprise, practitioner, and individuals). User identification is required for performing tests and accessing to historical data of the user. In one embodiment, biometric data is used for user authentication, for example, facial features, fingerprints, voices, heartbeats, vein recognition, etc. In another embodiment, a password is used for user authentication.

Figure 9:
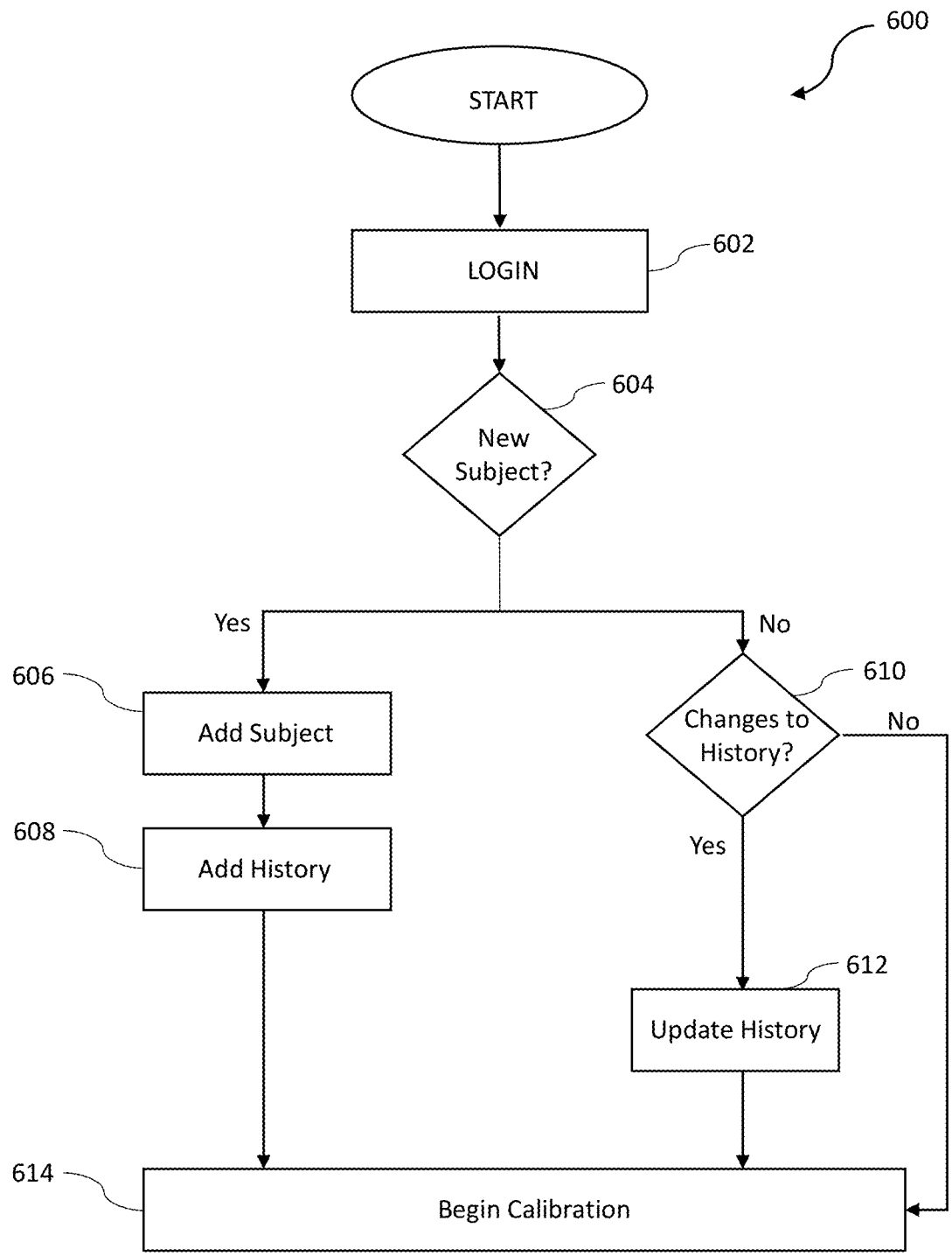
FIG. 9 is a flow chart detailing a method of logging into the server platform and updating subject information according to one embodiment of the present invention.

FIG. 9 is a flow chart detailing a method 600 of logging into the server platform and updating subject information. The user logs into the server platform in step 602. It is determined whether the subject is a new subject in step 604. If the subject is a new subject, the new subject is added to the database in step 606. A history for the new subject is added to the database in step 608 and the user begins calibration in step 614. If the subject is not a new subject, it is determined whether there are changes to a history for the subject in step 610. If there are changes to the history for the subject, the history is updated in step 612 before the user begins calibration in step 614. If there are not changes to the history in step 610, the user begins calibration in step 614.

The server platform is preferably operable to automatically transmit at least one report to the subject and/or to the at least one computing device. Additionally, the server platform is operable to bill the subject and create appointments.

In one embodiment, the application program installed on a mobile device and/or the server platform is operable to calculate a compatibility score of an element for a specific user based on historical data stored. In one embodiment, the compatibility score indicates a degree of effectiveness, a degree of sensitivity, a degree of tolerance, and/or a tendency to toxicity for the specific user, each of which is in a range between 0 and 4. In one example, wild salmon is given a degree of effectiveness of 4 and farmed salmon is given a degree of effectiveness of 2 because the ratio of Omega-3:Omega-6 is higher in wild salmon than farmed salmon. In another example, food sensitives are given a range between 0 and 4, wherein 0 indicates no food sensitivity, 1 indicates a food sensitivity, and 4 indicates highly allergic. In one embodiment, the score is in a range between −7 and 17 by weighing the effectiveness, sensitivity, tolerance, and toxicity. In another embodiment, the score is in a range between −7 and 19. In yet another embodiment, the score is in a range between −10 and 20. The higher the score is, the better it is for the specific user. Negative scores indicate potential damage and/or threats to a specific user. For example, pain relievers harm the kidneys, even though they are effective to reduce pain. In one example, a toxic element is given a score of −2, an average remedy is given a score of between 4 and 7, and an excellent remedy is given a score of between 10 and 19. The application program is operable to recognize the elements with a barcode scan or through image recognition via the mobile device.

In one embodiment, the server platform provides training programs for users. A user accesses the training programs by logging in to their account. In one embodiment, the training program is a pre-recorded demonstration or tutorial. In another embodiment, the training program is AI-powered and operable to verbally instruct a user for a testing step by step. The training program provides test reproducibility and enables mass adoption.

Figure 10:
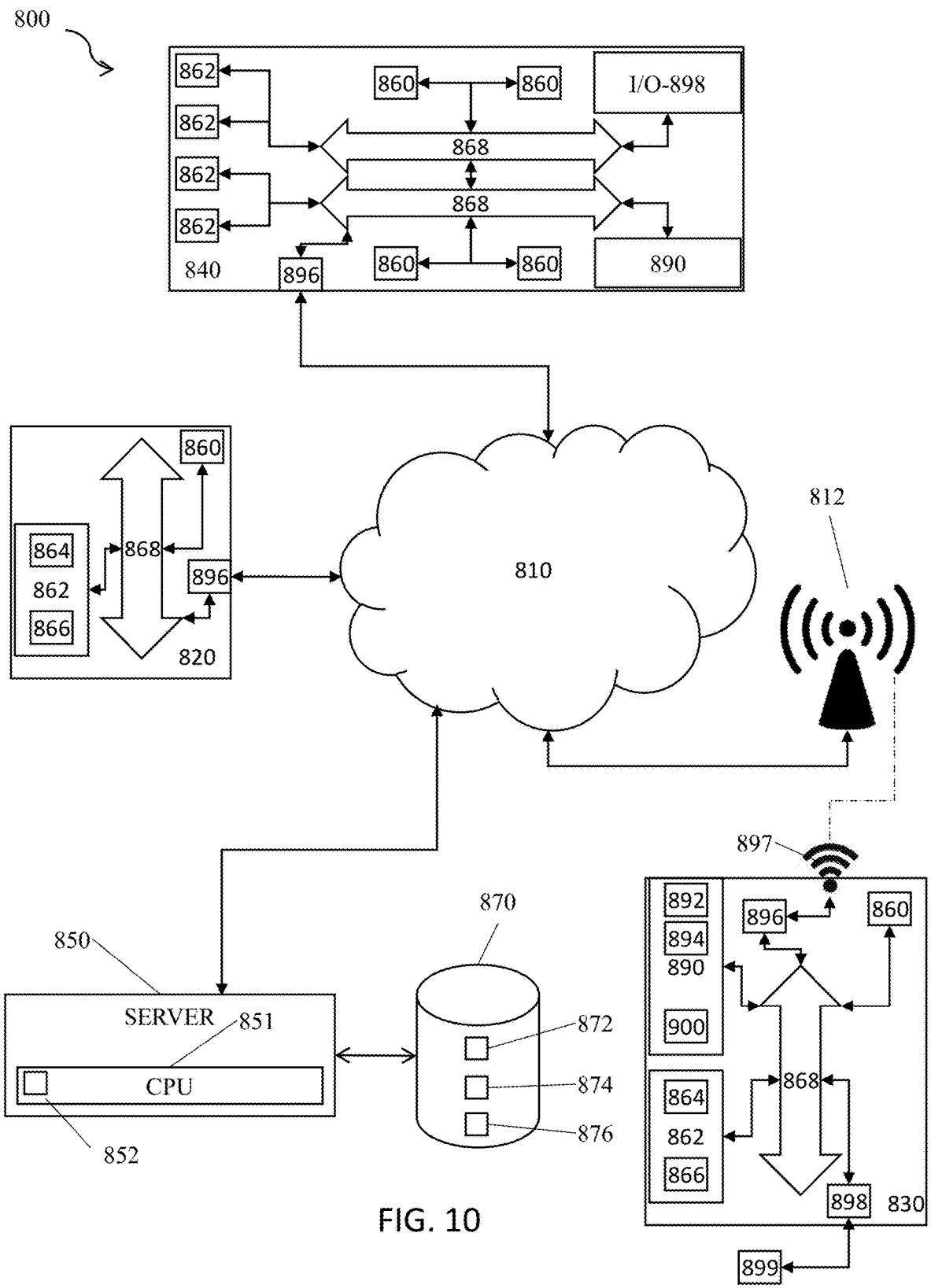
FIG. 10 is a schematic diagram of a cloud-based system of the present invention according to one embodiment of the present invention.

FIG. 10 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a cloud-based network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 10, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840, 850 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and are operable to be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which are operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 is operable to not include all of the components shown in FIG. 10, is operable to include other components that are not explicitly shown in FIG. 10, or is operable to utilize an architecture completely different than that shown in FIG. 10. The various illustrative logical blocks, modules, elements, circuits, and algorithms described in connection with the embodiments disclosed herein are operable be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the electrical conductivity meter can be a traditional electrical conductivity meter or a smart electrical conductivity meter. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A system for measuring galvanic skin response, comprising:
 an electrical conductivity meter electrically connected to a positive electrode and a negative electrode; and
 wherein the electrical conductivity meter is configured to communicate with a platform including a processor and a memory;
 wherein a circuit is created between the electrical conductivity meter and a point on a subject, wherein the circuit includes the positive electrode and the negative electrode;
 wherein the electrical conductivity meter is configured to measure the galvanic skin response of the subject;
 wherein the positive electrode includes a pressure sensor configured to indicate an amount of pressure applied by a tip of the positive electrode on the point of the subject; and
 wherein the platform is configured to detect variations in the pressure applied by the tip of the positive electrode on the point of the subject during a single session of testing, across multiple sessions of testing with a single subject, or across multiple sessions of testing with multiple subjects.

2. The system of claim 1, wherein the positive electrode includes an accelerometer configured to measure a position of the positive electrode.

3. The system of claim 1, wherein the platform utilizes artificial intelligence (AI) to detect the variations in the pressure applied by the positive electrode during the single session, across the multiple sessions with the single subject, or across the multiple sessions with the multiple subjects.

4. The system of claim 1, further including a hydration sensor to measure a level of hydration of the subject.

5. The system of claim 1, wherein the platform is configured to generate at least one report.

6. The system of claim 1, further comprising a graphical user interface (GUI) configured to toggle between menu items, record testing data, display results, display recommended treatment plans, and/or display at least one report.

7. The system of claim 1, wherein the circuit further includes at least one element in contact with a test plate of the electrical conductivity meter, wherein the at least one element is a food, a food component, a beverage, a supplement, a medication, a drug, an herb, a spice, a vitamin, a mineral, a gemstone, a metal, an electronic device, a bodily fluid, a tissue, and/or a hair sample.

8. The system of claim 7, wherein the test plate includes a plurality of cylindrical holes drilled in to the test plate configured to hold an ampule or a vial of the at least one element.

9. The system of claim 7, wherein one or more of the at least one element is labeled with a bar code or a passive radio frequency identification (RFID) tag.

10. The system of claim 7, wherein the platform is configured to calculate a compatibility score for the at least one element and the subject.

11. The system of claim 10, wherein the compatibility score indicates a degree of effectiveness, a degree of sensitivity, a degree of tolerance, and/or a tendency to toxicity.

12. A system for measuring galvanic skin response, comprising:
    an electrical conductivity meter electrically connected to a positive electrode and a negative electrode; and
    at least one element in contact with a test plate of the electrical conductivity meter, wherein the at least one element is a food, a food component, a beverage, a supplement, a medication, a drug, an herb, a spice, a vitamin, a mineral, a gemstone, a metal, an electronic device, a bodily fluid, a tissue, and/or a hair sample;
    wherein a circuit is created between the electrical conductivity meter, a point on a subject, and the at least one element in contact with the test plate, wherein the circuit includes the positive electrode and the negative electrode;
    wherein the electrical conductivity meter is configured to measure the galvanic skin response of the subject; and
    wherein a computing device is configured to calculate a compatibility score for the at least one element and the subject.

13. The system of claim 12, wherein the compatibility score indicates a degree of effectiveness, a degree of sensitivity, a degree of tolerance, and/or a tendency to toxicity.

14. The system of claim 12, wherein the positive electrode includes an accelerometer configured to measure a position of the positive electrode.

15. The system of claim 12, further including a hydration sensor to measure a level of hydration of the subject.

16. The system of claim 12, wherein the test plate includes a plurality of cylindrical holes drilled in to the test plate configured to hold an ampule or a vial of the at least one element.

17. The system of claim 12, wherein one or more of the at least one element is labeled with a bar code or a passive radio frequency identification (RFID) tag.

18. A system for measuring galvanic skin response, comprising:
    an electrical conductivity meter electrically connected to a positive electrode and a negative electrode; and
    at least one element in contact with a test plate of the electrical conductivity meter, wherein the at least one element is a food, a food component, a beverage, a supplement, a medication, a drug, an herb, a spice, a vitamin, a mineral, a gemstone, a metal, an electronic device, a bodily fluid, a tissue, and/or a hair sample;
    wherein a circuit is created between the electrical conductivity meter, a point on a subject, and the at least one element in contact with the component, wherein the circuit includes the positive electrode and the negative electrode; and
    wherein the electrical conductivity meter is configured to measure the galvanic skin response of the subject.

19. The system of claim 18, further including a hydration sensor to measure a level of hydration of the subject.

* * * * *